United States Patent [19]
Hedberg et al.

[11] Patent Number: 4,723,551
[45] Date of Patent: Feb. 9, 1988

[54] ATRIUM-CONTROLLED HEART PACEMAKER

[75] Inventors: Sven-Erik Hedberg, Kungsängen; Anders Lindgren, Täby, both of Sweden

[73] Assignee: Siemens Aktiengesellschaft, Berlin and Munich, Fed. Rep. of Germany

[21] Appl. No.: 910,997

[22] Filed: Sep. 24, 1986

[30] Foreign Application Priority Data

Oct. 4, 1985 [DE] Fed. Rep. of Germany ....... 3535517

[51] Int. Cl.⁴ .............................................. A61N 1/36
[52] U.S. Cl. .............................................. 128/419 PG
[58] Field of Search .................................. 128/419 PG

[56] References Cited

U.S. PATENT DOCUMENTS

| | | | |
|---|---|---|---|
| 4,181,133 | 1/1980 | Kolenik et al. | 128/419 PG |
| 4,280,502 | 7/1981 | Baker, Jr. et al. | 128/419 PG |
| 4,284,082 | 8/1981 | Funke et al. | 128/419 PG |
| 4,307,725 | 12/1981 | Sowton et al. | 128/419 PG |
| 4,390,021 | 6/1983 | Spurrell et al. | 128/419 PG |
| 4,408,606 | 10/1983 | Spurrell et al. | 128/419 PG |
| 4,429,697 | 2/1984 | Nappholz et al. | 128/419 PG |
| 4,467,810 | 8/1984 | Vollmann | 128/419 PG |
| 4,485,818 | 12/1984 | Leckrone et al. | 128/419 PG |
| 4,515,161 | 5/1985 | Wittkampf et al. | 128/419 PG |
| 4,541,430 | 9/1985 | Elmquist et al. | 128/419 PG |
| 4,543,963 | 10/1985 | Gessman | 128/419 PG |
| 4,574,437 | 3/1986 | Segerstad et al. | 128/419 PG |

FOREIGN PATENT DOCUMENTS

8203781 11/1982 Fed. Rep. of Germany ...... 128/419 PG

Primary Examiner—William E. Kamm
Assistant Examiner—Timothy J. Keegan
Attorney, Agent, or Firm—Hill, Van Santen, Steadman & Simpson

[57] ABSTRACT

An atrium-controlled heart pacemaker has a monitoring circuit for interrupting tachycardia which may be generated by the pacemaker. The monitoring circuit includes a P-wave counter and a window generator connected thereto. The window generator prescribes a window for the P-wave counter within which a predetermined maximum number n of P-waves is allowed to appear. When the $n^{th}$ P-wave appears in the window, forwarding of the $n+1^{th}$ P-wave to the stimulation circuit is blocked.

5 Claims, 1 Drawing Figure

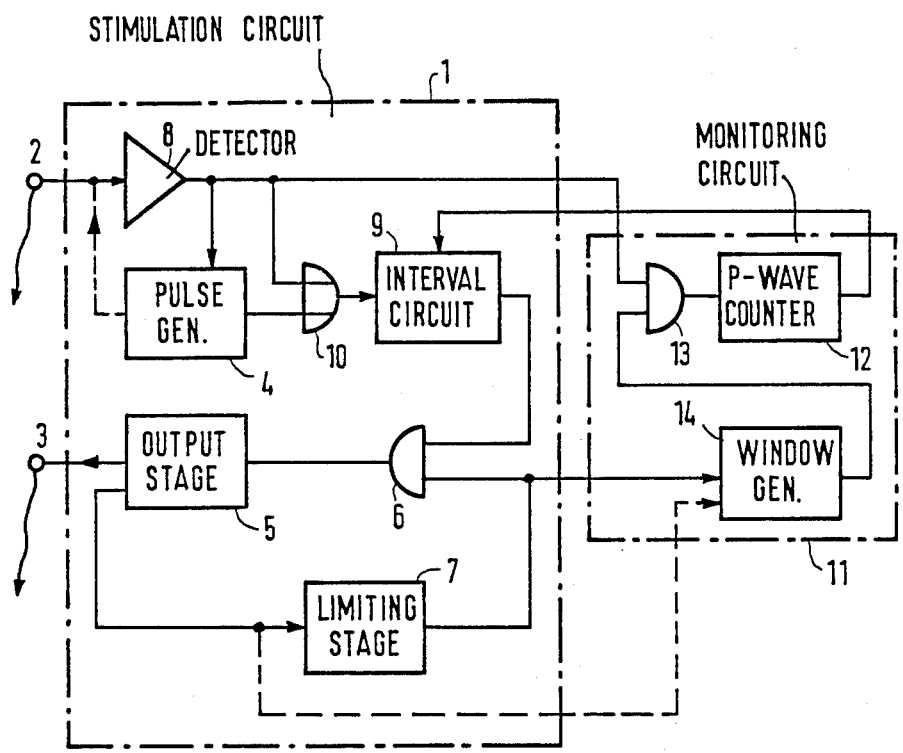

ATRIUM-CONTROLLED HEART PACEMAKER

BACKGROUND OF THE INVENTION

The present invention relates to atrium-controlled heart pacemakers. Such pacemakers generally include a pulse generator operating synchronously with the heart P-waves. The pulse generator operates continuously between a programmed base frequency and a maximum frequency. In pacemakers of this type, a closed loop is sometimes created by the atrial lead and detector, the ventricular output stage and a lead retrograde conduction path in the heart tissue from the ventricle to the atrium. Such a closed loop presents conditions under which pacemaker-induced tachycardia may occur.

It is an object of the present invention to provide an atrium-controlled heart pacemaker wherein pacemaker-induced tachycardia may be automatically terminated.

The above object is achieved in accordance with the principles of the present invention by an atrium-controlled heart pacemaker which includes a monitoring circuit for the stimulation circuit which interrupts forwarding of the P-wave to the stimulation circuit when the frequency of P-waves exceeds a predetermined value. The monitoring circuit includes a window generator which sets a window within which a predetermined maximum number n of P-waves are allowed to occur. When the $n^{th}$ P-wave occurs within the window, this is an indication that tachycardia induced by the heart pacemaker is present. Under such circumstances, the generation of a stimulation pulse on the basis of the next P-wave acquired by the atrium electrode is suppressed, and thus the closed circuit is interrupted and the tachycardia may be terminated.

DESCRIPTION OF THE DRAWINGS

The single FIGURE shows a schematic block diagram of a heart pacemaker constructed in accordance with the principles of the present invention.

DESCRIPTION OF THE PREFERRED EMBODIMENTS

The elements of a heart pacemaker constructed in accordance with the principles of the present invention which are necessary to explain the operation thereof are schematically shown in the drawing. The pacemaker includes a stimulation circuit 1 and a monitoring circuit 11.

The stimulation circuit 1 includes an input 2 for atrial signals and an output 3 for ventricular stimulation signals. Generation of stimulation pulses is undertaken by a pulse generator 4 which is synchronized by the incoming P-waves at the input 2 and which supplies the stimulation pulses through an output stage 5. A limiting stage 7 is connected to the output stage 5 through an AND gate 6. The limiting stage 7 defines the highest synchronous rate for the heart pacemaker which may be, for example, approximately 150 pulses per minute. The stimulation circuit 1 further includes a detector 8 for resetting the pulse generator 4 and an interval circuit 9 which is connected to the detector 8 and to the pulse generator 4 through an OR gate 10.

The monitoring circuit 11 includes a P-wave counter which is connected to the detector 8 and to a window generator 14 through an AND gate 13. The input of the window generator 14 is connected to the output of the limiting stage 7.

The window generator 14 prescribes the window for the P-wave counter 12 within which a predetermined maximum number (n) of P-waves is allowed to appear. When the number n is reached, the $n+1^{th}$ P-wave is blocked by the interval circuit 9, and the normally closed circuit is opened, so that tachycardia may be terminated.

Operation of the circuit is as follows.

A P-wave which is detected by the detector 8 resets the time base unit in the pulse generator 4 when it lies outside of the atrial refractory time. The detector signal is forwarded to the interval circuit 9 which starts an AV interval. At the end of the AV interval, a signal reaches the output stage 5, so that a stimulation pulse is supplied to the ventricle.

The limiting stage 7 limits the frequency of the heart pacemaker to a maximum synchronous rate (HSR). If the limiting stage 7 is activated when the signal supplied to the output stage 5 arrives, the AND gate 6 does not permit the signal from the interval circuit 9 to pass to the output stage 5 until enabled by the limiting stage 7. The limiting stage 7 receives a pulse from the output stage 5 when a stimulation pulse is emitted, which starts an HSR interval. Pacemaker operation in this manner is known.

In accordance with the principles of the present invention, the time function is started in the window generator 14 when the limiting stage 7 is activated. A window is formed lasting a defined time after this activation. When a P-wave is detected during this time, the P-wave counter 12 is incremented by one count. When the P-wave counter 12 has reached the $n+1^{th}$ stage, the AV interval which would normally occur following the $n+1^{th}$ P-wave is interrupted. The P-wave counter 12 is then reset to zero. The $n+1^{th}$ P-wave thus does not cause a ventricular stimulation pulse and the entire circuit is switched back to its original condition.

Although modifications and changes may be suggested by those skilled in the art it is the intention of the inventors to embody within the patent warranted hereon all changes and modifications as reasonably and properly come within the scope of their contribution to the art.

We claim as our invention:

1. An atrium-controlled heart pacemaker comprising:
   means for sensing a P-wave in the atrium of a heart;
   means for normally supplying a ventricular stimulation pulse to said heart following a sensed P-wave in said atrium; and
   means connected to said means for sensing and to said means for supplying ventricular pulses for interrupting said means for supplying ventricular pulses when the frequency of the sensed P-waves exceeds a predetermined value such that no ventricular stimulation pulse is supplied to said heart.

2. A heart pacemaker as claimed in claim 1, wherein said means for interrupting includes:
   a P-wave counter connected to said means for sensing for counting the number of sensed P-waves in said atrium; and
   means for setting a time window connected to said P-wave counter, said means for setting a time window enabling said P-wave counter to count said P-waves only during said window.

3. A heart pacemaker as claimed in claim 2, wherein said means for setting a time window is also connected to said means for supplying ventricular pulses, and wherein said means for setting a time window commences said time window upon the occurrence of each ventricular pulse.

4. A heart pacemaker as claimed in claim 2, wherein said means for supplying ventricular pulses includes an interval circuit connected to said means for sensing said interval circuit generating a pulse for initiating supply of a ventricular pulse after the occurrence of a sensed P-wave in said atrium, and wherein said P-wave counter is connected to said interval circuit for normally enabling said interval circuit and for disenabling said interval circuit when said prescribed P-wave frequency is exceeded.

5. A heart pacemaker as claimed in claim 1, wherein said prescribed P-wave frequency corresponds to n P-waves, and wherein said means for interrupting includes means for setting a time window, and wherein said means for interrupting interrupts said means for supplying said ventricular pulses upon the occurrence of an $n+1^{th}$ P-wave in said time window.

* * * * *